United States Patent [19]

Voda

[11] Patent Number: 5,462,561
[45] Date of Patent: Oct. 31, 1995

[54] SUTURE DEVICE

[76] Inventor: Jan K. Voda, 1404 Camden Way, Oklahoma City, Okla. 73116

[21] Appl. No.: 102,575

[22] Filed: Aug. 5, 1993

[51] Int. Cl.⁶ .................................................. A61B 17/00
[52] U.S. Cl. ........................ 606/144; 606/148; 606/232; 112/169
[58] Field of Search ............................... 606/139, 144, 606/145, 147, 148, 232, 225; 112/169, 80.03

[56]  References Cited

U.S. PATENT DOCUMENTS

| | | | |
|---|---|---|---|
| 3,123,077 | 3/1964 | Alcamo . | |
| 3,253,594 | 5/1966 | Matthews et al. . | |
| 3,470,875 | 10/1969 | Johnson | 606/145 |
| 3,543,758 | 12/1970 | McWhorter . | |
| 3,543,759 | 12/1970 | McWhorter . | |
| 3,871,379 | 3/1975 | Clarke | 606/148 |
| 4,077,412 | 3/1978 | Moossun . | |
| 4,182,341 | 1/1980 | Perri | 606/225 |
| 4,345,601 | 8/1982 | Fukuda | 606/147 |
| 4,367,740 | 1/1983 | Evanoski, III | 604/43 |
| 4,493,323 | 1/1985 | Albright et al. | 606/144 |
| 4,587,969 | 5/1986 | Gillis . | |
| 4,666,433 | 5/1987 | Parks | 604/178 |
| 4,669,473 | 6/1987 | Richards et al. . | |
| 4,725,264 | 2/1988 | Glassman | 604/102 |
| 4,744,364 | 5/1988 | Kensey . | |
| 4,798,592 | 1/1989 | Parks | 604/49 |
| 4,829,994 | 5/1989 | Kurth . | |
| 4,852,568 | 8/1989 | Kensey . | |
| 4,890,612 | 1/1990 | Kensey | 606/213 |
| 4,929,246 | 5/1990 | Sinofsky | 606/8 |
| 5,009,639 | 4/1991 | Keymling | 604/96 |
| 5,021,059 | 6/1991 | Kensey | 606/213 |
| 5,037,433 | 8/1991 | Wilk et al. | 606/144 |
| 5,053,046 | 10/1991 | Janese | 606/215 |
| 5,074,874 | 12/1991 | Yoon et al. | 606/139 |
| 5,108,421 | 4/1992 | Fowler | 606/213 |
| 5,188,636 | 2/1993 | Fedotov | 606/144 |
| 5,281,234 | 1/1994 | Wilk et al. | 606/144 |
| 5,284,488 | 2/1994 | Sideris | 606/213 |
| 5,304,184 | 4/1994 | Hathaway et al. | 606/148 |
| 5,364,408 | 11/1994 | Gordon | 112/169 |

FOREIGN PATENT DOCUMENTS 0535906  4/1993  European Pat. Off. ............... 606/148

*Primary Examiner*—Stphen C. Pellegrino
*Assistant Examiner*—Jeffrey A. Schmidt
*Attorney, Agent, or Firm*—Dougherty, Hessin, Beavers & Gilbert

[57] ABSTRACT

An apparatus is provided for suturing a perforation in a side wall of a patient's blood vessel. The apparatus includes an outer sheath having a longitudinal passage defined therethrough. The outer sheath is adapted to be inserted through the perforation in the patient's blood vessel. The apparatus includes at least a first suture point and at least a first suture thread attached to said first suture point. A carrier device is provided for carrying the first suture point in a distal direction through the longitudinal passage of the outer sheath into the patient's blood vessel and for pulling the first suture point in a proximal direction through the side wall of the patient's blood vessel. At least two such suture points and suture threads are preferably so attached to the patient's blood vessel and are then utilized to close the perforation.

41 Claims, 7 Drawing Sheets

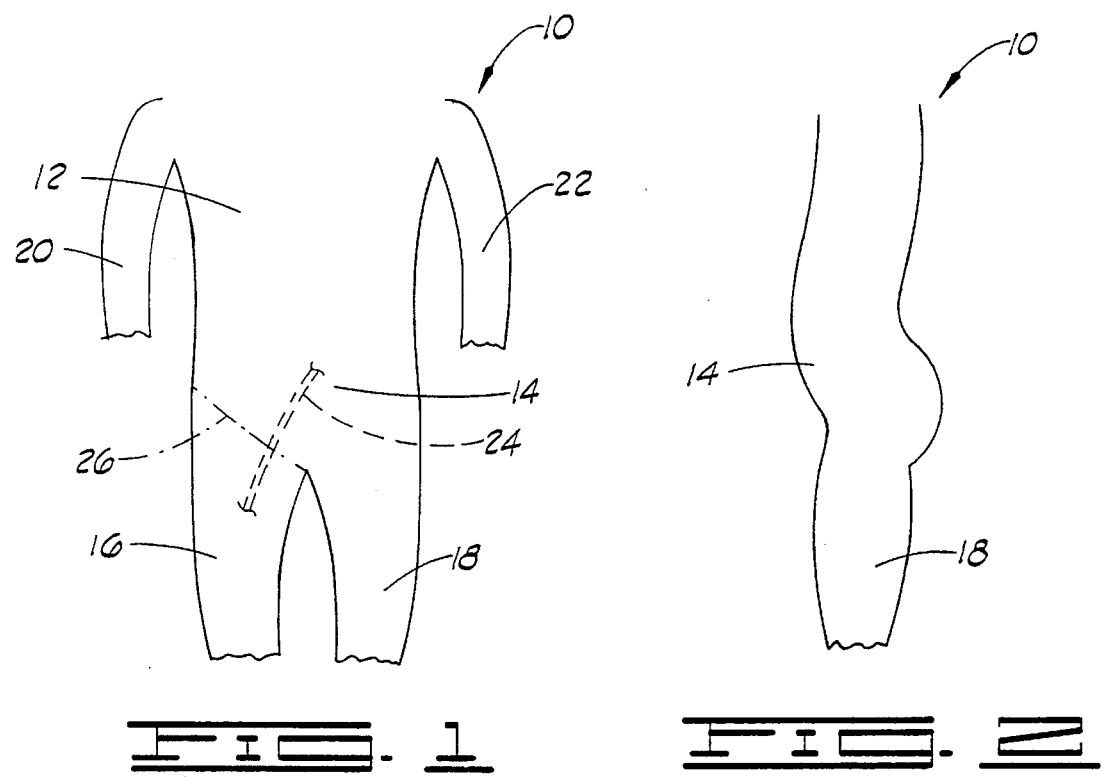
FIG. 1
FIG. 2
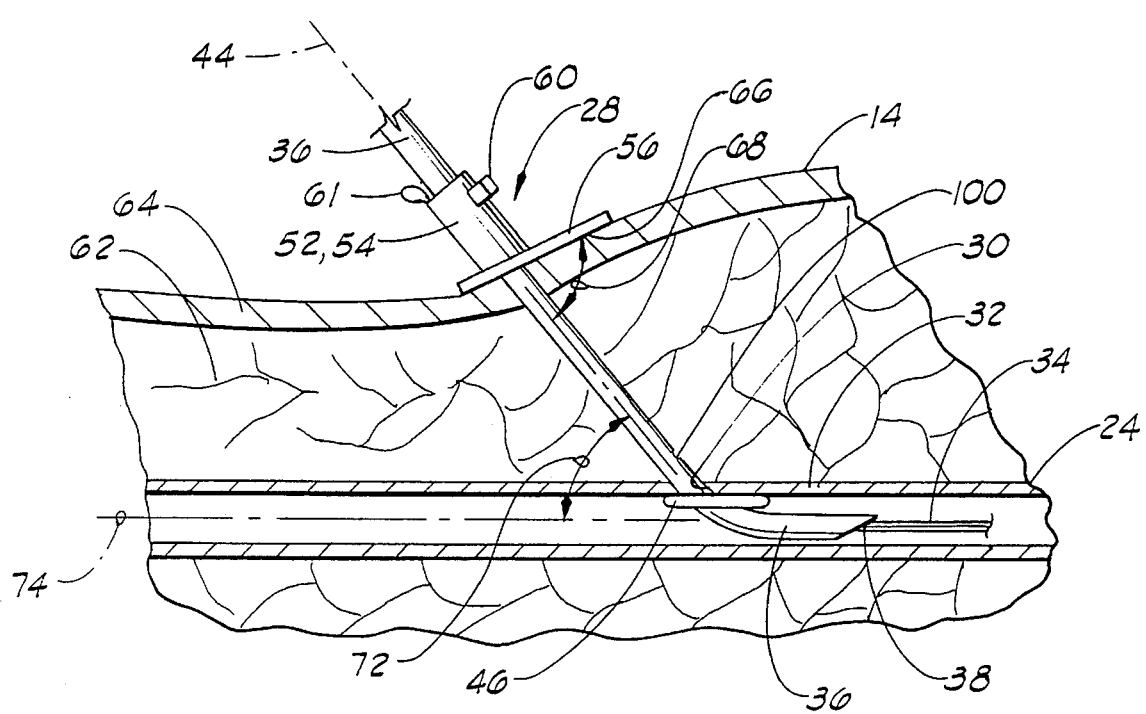
FIG. 3

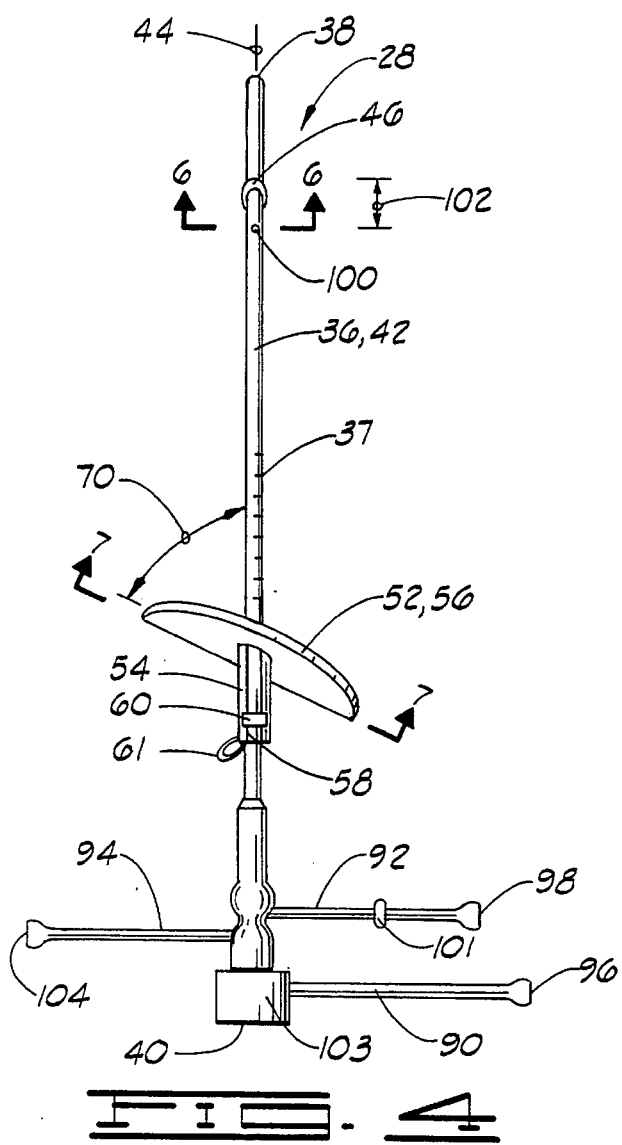
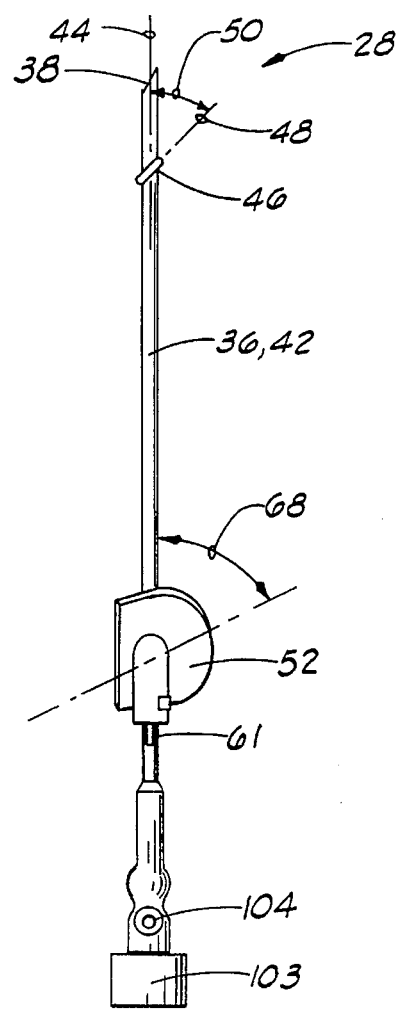
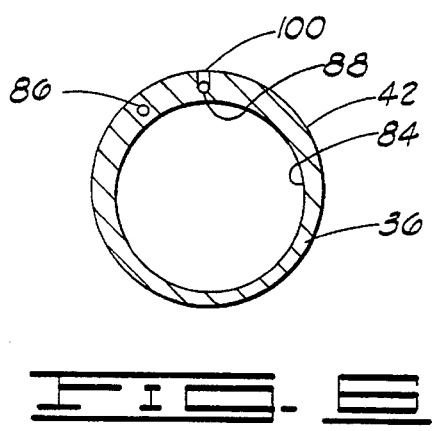
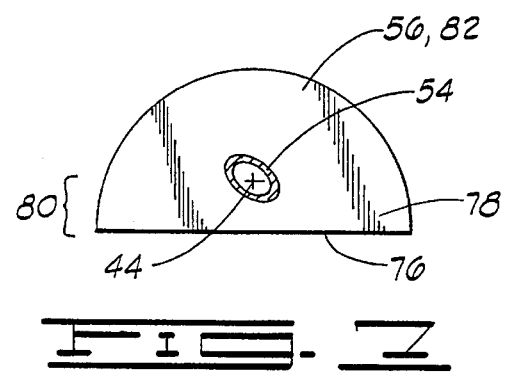

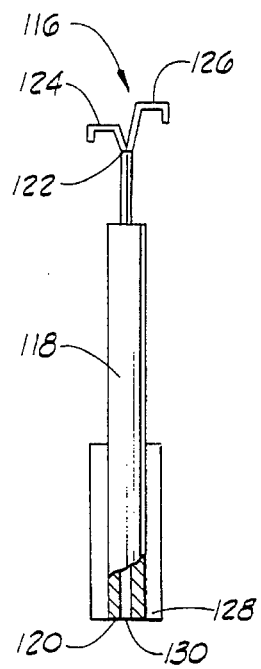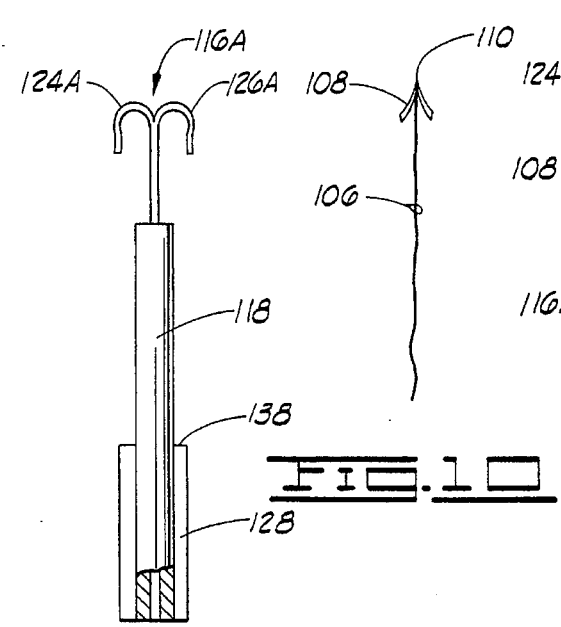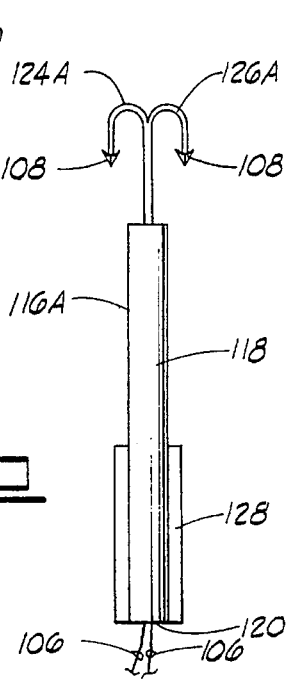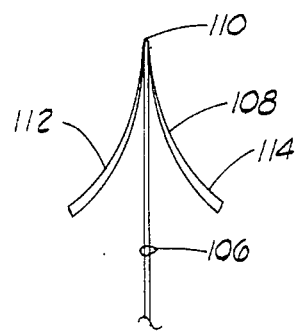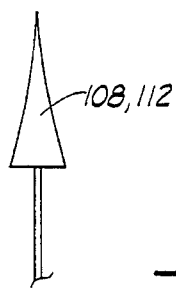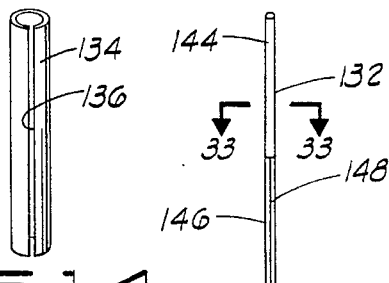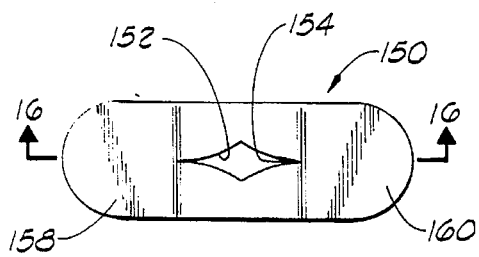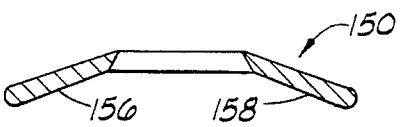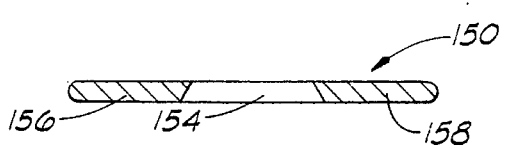

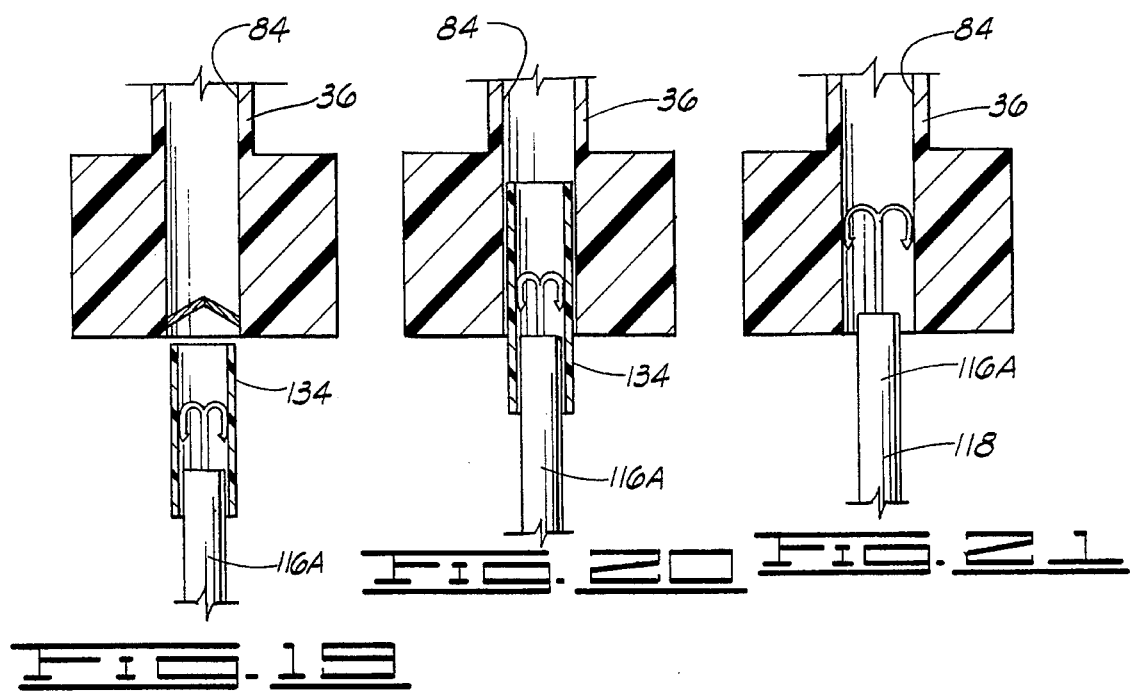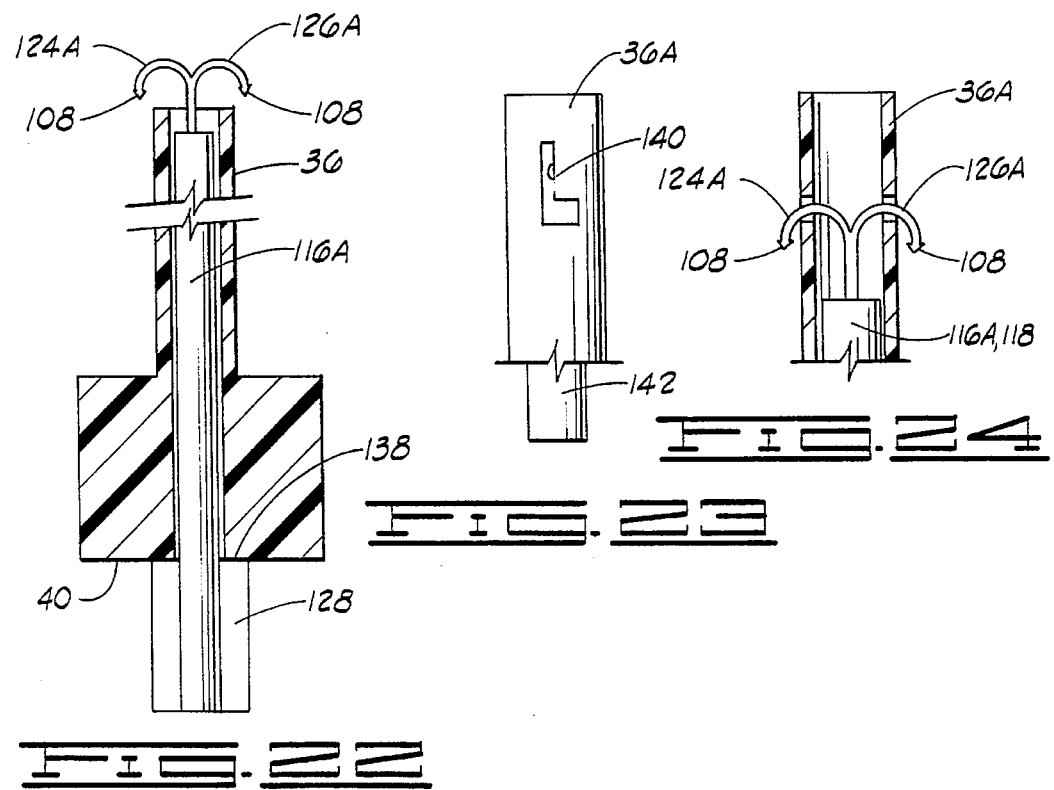

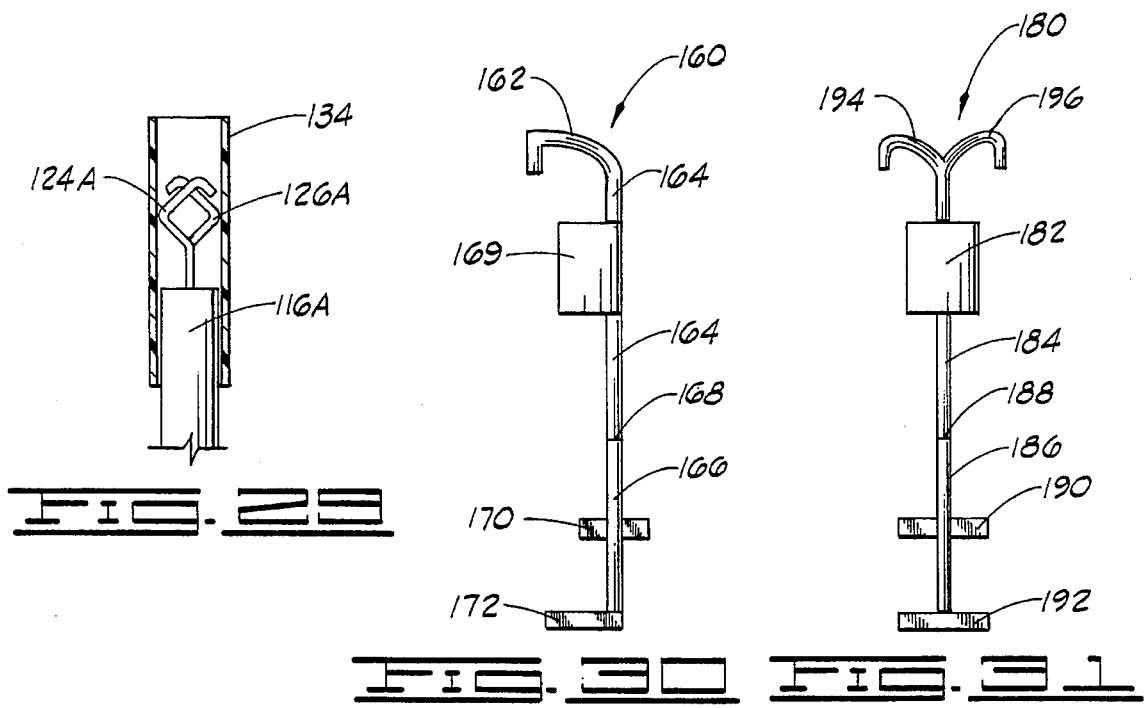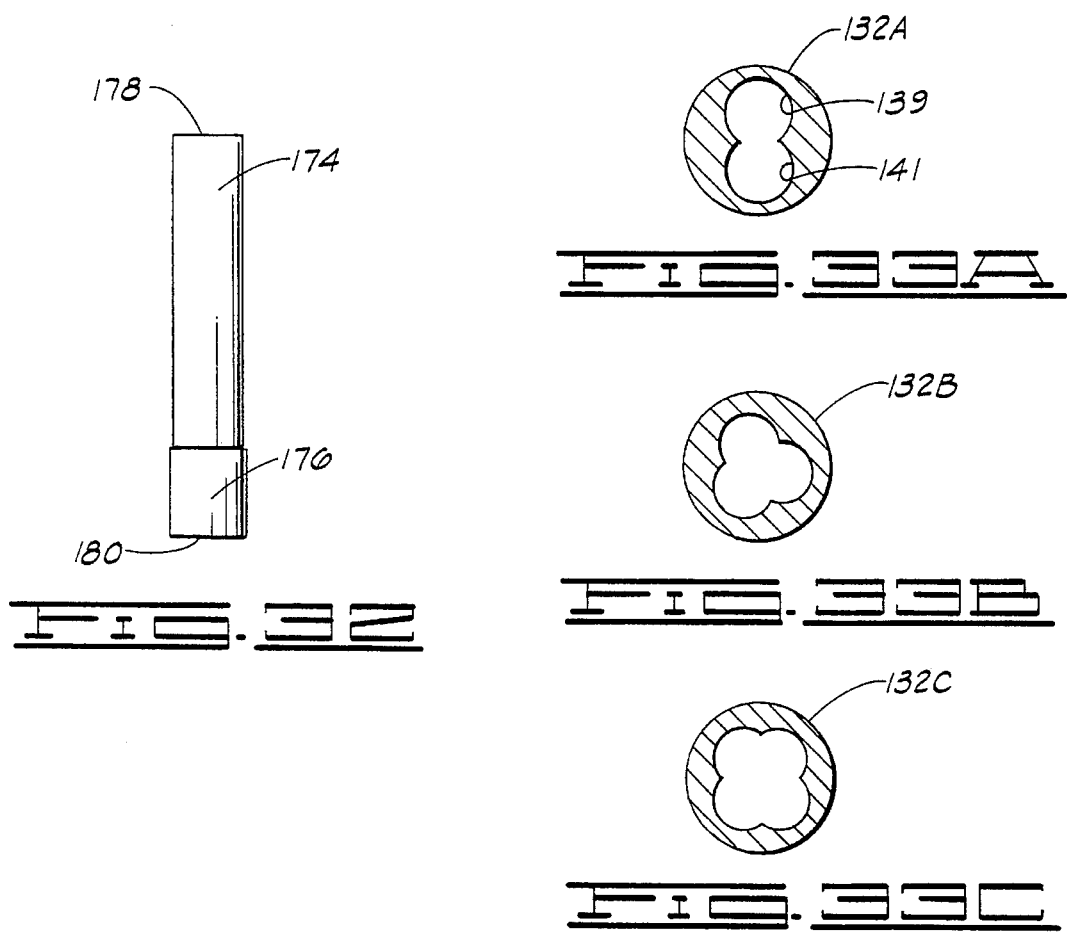

SUTURE DEVICE

BACKGROUND OF THE INVENTION

1. Field of the Invention

The present invention relates generally to apparatus and methods for closing a perforation in a blood vessel.

2. Description Of The Prior Art

In 1991, around 3,000,000 punctures of human arteries were performed in the United States alone. These punctures are usually done for diagnostic cardiac or radiological procedures and also for therapeutic procedures. Such procedures include coronary and peripheral angioplasties and insertion of devices such as intra-aortic balloon pumps.

The percutaneous puncture of the artery usually is performed by sticking the artery with a needle through which a guide wire is inserted. Over this guide wire a dilator is advanced into the artery, and a sheath is often mounted onto the dilator. The dilator is then removed and the distal end of the sheath is left inside the lumen of the artery. A small proximal segment of the sheath is left outside of the artery and outside of the skin of the patient. This proximal segment of the sheath usually contains a hemostatic valve to prevent bleeding from the artery through the sheath.

Sheaths currently in use are typically flexible having one thin wall. They are usually removed from the artery immediately after the procedure or within several hours.

In recent years, the practice has developed of treating many patients with anticoagulation medication such a Heparin. The presence of the anticoagulation medication in the patient's system, of course, exacerbates problems of bleeding.

One particular problem encountered during such surgical procedures is bleeding from the perforation after the surgical procedure is completed and the sheath is removed. This has typically been addressed in the prior art by applying pressure to the location of the perforation for twenty to thirty minutes and then requiring the patient to lie immobile for many hours.

One frequent complication of this prior art procedure is that subsequent bleeding from the punctured artery results in collection of blood, i.e., hematoma, in the subcutaneous tissue. The hematomas are usually not large but do require several weeks to heal completely. Less frequently, the hematomas are large and create serious problems. The patient may have to be transfused, and the puncture area will be uncomfortable thus limiting the patient's activities. On rare occasions, a so-called pseudoaneurysm can develop, which is a space between the lumen of the artery and subcutaneous tissue space. These often have to be surgically repaired.

The present invention is directed to a suture device which is capable of closing the puncture opening in the artery when the sheath is removed, thus eliminating these problems.

SUMMARY OF THE INVENTION

The present invention provides an apparatus for suturing a perforation in a side wall of the patient's blood vessel. The apparatus includes an outer sheath having a longitudinal passage defined therethrough. The outer sheath is adapted to be inserted through the perforation in the patient's blood vessel.

The apparatus preferably includes first and second suture points and first and second suture threads attached to said first and second suture points.

A carrier device is provided for carrying the suture points in a distal direction through the elongated passage of the outer sheath into the patient's blood vessel and for pulling the suture points in a proximal direction through the side wall of the patient's blood vessel.

Means are also provided for subsequently pulling the two suture threads together to close the perforation.

Numerous objects, features and advantages of the present invention will be readily apparent to those skilled in the art upon a reading of the following disclosure when taken in conjunction with the accompanying drawings.

BRIEF DESCRIPTION OF THE DRAWINGS

FIG. 1 is a schematic view of the front of a human patient showing in dashed lines the approximate location of the femoral artery and showing in phantom lines the approximate location of the right groin crease between the patient's right leg and abdomen.

FIG. 2 is a right-side view of FIG. 1, which may also be said to be a view of the patient's left side, illustrating a typical patient physique having a somewhat protruding abdomen.

FIG. 3 is a schematic, sectioned view showing the location of the arterial sheath of the present invention in place within a patient's femoral artery with a clamping device attached to a proximal portion of the sheath. The clamping device is located in the right groin crease of the patient and engages the lower abdominal wall of the patient.

FIG. 4 is a plan view of the arterial sheath of the present invention.

FIG. 5 is a left-side view of the sheath of FIG. 4.

FIG. 6 is a sectioned view taken along line 6—6 of FIG. 4 showing the internal passages of the sheath.

FIG. 7 is an elevation view taken along line 7—7 of FIG. 4 showing the shape of the clamping shield of the sheath.

FIG. 8 is a plan view of one embodiment of a carrier device for carrying a suture through the sheath of FIGS. 4–7 to aid in closing of the perforation in the artery after removal of the sheath.

FIG. 9 is a plan view of a second embodiment of a suture carrier.

FIG. 10 is a plan view of a suture thread having a suture point attached thereto.

FIG. 11 is a plan view of a suture carrier like that of FIG. 9 with two suture threads and suture points like that of FIG. 10 installed therein.

FIG. 12 is an enlarged plan view of the suture point and attached suture thread of FIG. 10.

FIG. 13 is a right-side view of the suture point and attached suture thread of FIG. 12.

FIG. 14 is a plan view of a split cylindrical intermediate sheath used to insert the carrier device of FIG. 8 or FIG. 9 into the sheath of FIGS. 4–7.

FIG. 15 is a plan view of a fastening disc used to pull together the two sutures after they are placed in the patient's blood vessel.

FIG. 16 is a sectioned view taken along line 16—16 of FIG. 15 showing the configuration of the fastening disc prior to the time the disc is attached to the tensioned suture threads.

FIG. 17 is a view similar to FIG. 16 showing the manner in which the fastening disc tends to flatten out when attached to the tensioned suture threads.

FIG. 18 is a plan view of a fastening tube which may be used with or instead of the fastening disc of FIG. 15 to aid in pulling the suture threads together to close the perforation in the patient's artery.

FIGS. 19–22 comprise a sequential series of drawings showing the manner in which the suture carrier and sutures of FIG. 11 are inserted into the sheath of FIGS. 4–7 and subsequently positioned within the interior of the blood vessel.

FIG. 23 is a plan view of a modified sheath having two diametrically opposed L-shaped guide slots for receiving and supporting the expandable arms of the carrier device.

FIG. 24 is similar to FIG. 22 and shows the suture carrier in place within the sheath of FIG. 23.

FIG. 29 is a view similar to the lower portion of FIG. 19 showing an alternative manner in which the expandable arms may be folded up within the insertion sheath.

FIG. 30 is a plan view of another embodiment of a carrier device constructed for carrying one suture at a time through the sheath.

FIG. 31 is a plan view of still another embodiment of a suture carrier.

FIG. 32 is a plan view of an alternative form of an insertion sheath.

FIGS. 33A, 33B and 33C are cross-sectional views of alternative forms of the fastening tube of FIG. 18. These views are taken along line 33—33 of FIG. 18.

DETAILED DESCRIPTION OF THE PREFERRED EMBODIMENTS

Figure 25:
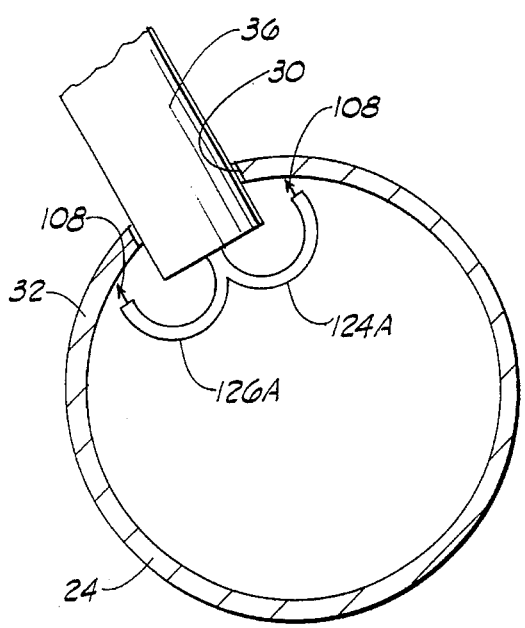
FIGS. 25–28 comprise a sequential series of sketches showing a cross-section through the blood vessel at the perforation and showing the manner in which the sheath and carrier device assembly of FIGS. 19–22 is utilized to place the sutures through the vessel wall on opposite sides of the perforation and to subsequently close the perforation.

FIGS. 1 and 2 depict in schematic form the body of a human patient which is generally designated by the numeral 10. FIG. 1 is a frontal view of the patient, and could be considered to be a plan view of the patient lying on his back. The patient's chest 12, abdomen 14, right leg 16, left leg 18, right arm 20, and left arm 22 are depicted.

In dashed lines designated by the numeral 24, the approximate position of the patient's femoral artery is illustrated. In phantom lines designated by the numeral 26, the location of the patient's right groin crease is illustrated.

FIG. 2 is a view of the patient's left side illustrating a typical physique wherein the abdomen 14 protrudes somewhat relative to the groin crease. The geometry of a given patient of course is dependent upon the patient's particular physique and degree of corpulence.

FIG. 3 is a schematic, sectioned view illustrating a vascular sheath apparatus generally designated by the numeral 28, placed through a perforation 30 in a side wall 32 of the patient's blood vessel 24 for placement of a catheter or other medical device 34 in the patient's blood vessel 24. The interior of the vessel 24 may be generally referred to as a cavity 24 in the patient's body. The details of construction of the vascular sheath apparatus 28 are best shown in FIGS. 4– 7.

The vascular sheath apparatus 28 includes an elongated cylindrical outer sheath 36 having a distal end 38 and a proximal end 40. The outer sheath 36 has a generally cylindrical outer surface 42 and has a longitudinal axis 44. As seen in FIG. 3, the distal end portion of sheath 36 adjacent distal end 38 is adapted to be received through the perforation 30 and in the blood vessel 24. The sheath 36 is flexible and bends when it enters vessel 24, as seen in FIG. 3.

Distal end 38 preferably is beveled at an angle of approximately 45° as seen in FIGS. 3 and 5. It may also, however, be blunt.

The sheath 36 preferably has gradations or other indicia 37 defined thereon to indicate the exact depth of insertion of the distal tip 38. Sheath 36 has a length in the range of 4 cm. to 40 cm., and a diameter in the range of from 4 French to 22 French, and preferably is in the range of from 6 French to 9 French. One French is equal to 0.33 mm.

The vascular sheath apparatus 28 includes an annular inflatable sealing balloon 46 disposed about the sheath 36 and expandable radially outward beyond the outer surface 42 of sheath 36. As best seen in FIG. 5, the sealing balloon 46 lies in a plane 48 oriented at an acute angle 50 to the longitudinal axis 44 of sheath 36. Angle 50 is preferably in the range of 30° to 60°, and more preferably is about 45°. The angle 50 results in an upper portion of the sealing balloon 46 being tilted in a distal direction. When the balloon 46 is inflated it should extend approximately two millimeters radially beyond the outer surface 42 of sheath 36.

The elliptical shape of balloon 46 and its slanting so that it will be generally parallel to the side wall of vessel 24 increases the stability of the sheath 36 and of the balloon 46 and decreases the chance for the balloon 46 to bend over or distort and allow the sheath 36 to be pulled through the perforation 30.

The material of balloon 46 can either be expandable or non-expandable material. Preferably, balloon 46 should withstand high pressures of, for example six to ten atmospheres or higher. It can be produced out of conventional materials such as those used for angioplasty balloons, for example, polyolefin, polyvinylchloride or PET material. It could also be produced out of more expandable material such as balloons used in what is known as the Swan Ganz catheter.

The vascular sheath apparatus 28 further includes a clamp 52 slidably disposed on the sheath 36 proximally of the sealing balloon 46. The clamp 52 includes a flexible split collar 54 slidably received about sheath 36, with a clamping plate 56 extending laterally from the collar 54. The collar 54 has a split 58 defined therein and has a latch or buckle 60 for securing the split collar 54 tightly upon the sheath 36 to lock the collar 54 and plate 56 in place relative to the sheath 36. The latch 60 may be generally described as a securing means 60 for securing the clamp 52 in position relative to the sheath 36. The cylinder 54 is two to three centimeters long and has a diameter of one to two centimeters.

When the split is open the device 52 can freely slide up and down the sheath 36. The buckle 60 can be closed thus closing the split 58 and causing the cylinder 54 to tightly grip the outer surface of the sheath 36 so that it cannot move. The cylinder 54 is preferably constructed from a material that has a relatively high coefficient of friction with the sheath 36 so that when the buckle 60 is fastened, the clamp 52 will not slide relative to the sheath 36.

A loop 61 is preferably provided on the proximal end of cylinder 54. After the clamp 52 is placed tightly adjacent the patient's skin as shown in FIG. 3, a suture (not shown) can be placed through loop 61 and attached to the skin 64 to aid in holding the clamp 52 in place.

As is best seen in FIG. 3, the clamp 52 and balloon 46 are so arranged and constructed that with the proximal end portion of the sheath 36 extending through the perforation 30 into the blood vessel 24 and with the sealing balloon 46 inflated inside the vessel 24, the clamp 52 is slidable along the sheath 36 toward the sealing balloon 46 to sandwich the vessel side wall 32 and the patient's body tissue 62 and outer skin 64 external of the blood vessel 24 between the sealing balloon 46 and the clamp 52 to reduce bleeding through the perforation 30 around the sheath 36.

The clamping plate 56 is preferably oriented in a skewed fashion relative to the longitudinal axis 44 of sheath 36 so that a proximally facing clamping surface 66 thereof will snugly engage a substantial portion of the patient's skin 64 as shown in FIG. 3 when the perforation 30 is formed adjacent the right groin crease 26 of the patient. It has been determined that a preferred orientation for the clamping plate 56 includes a tilting of the upper portion thereof in a distal direction and a tilting of the left-hand portion thereof as viewed in FIG. 4 in a distal direction. This can be described as tilting the clamping surface 66 relative to the longitudinal axis 44 at a first acute angle 68 in a vertical plane relative to longitudinal axis 64, and at a second acute angle 70 in a horizontal plane relative to the axis 44.

References to up, down, horizontal, vertical, etc., with relation to the longitudinal axis 44 are made in the context of the apparatus 28 being held with its longitudinal axis 44 horizontal and viewed from above as illustrated in FIG. 4. As is apparent in FIG. 3, the apparatus 28 is in fact typically tilted at an angle to the horizontal when it is in use, but it still in a preferred embodiment will have a characteristic top or upper surface and left- and right-hand sides due to the fact that it is preferably constructed to be received in the specific location indicated in FIG. 1 wherein the right groin crease 26 crosses the femoral artery 24.

The mentioned first acute angle 68 is preferably in a range of from about 30° to 90°, and more preferably is about 60°. The second acute angle 70 is preferably in a range of from about 45° to about 90°, and more preferably is approximately 60° which is approximately the angle of the right groin crease 26 to the femoral artery 24 where the femoral artery 24 passes beneath the right groin crease 26.

The angle 68 can be generally described as resulting in an upper portion of the planar clamping surface 66 being tilted in a distal direction. The angle 70 can be generally described as resulting in a left-hand side of the generally planar clamping surface being located distally of a right-hand side thereof for a viewer facing in a distal direction. Thus for a surgeon using the apparatus 28 and viewing it as seen in FIG. 4, the left-hand side of clamping plate 56 is located distally of the right-hand side of clamping plate 56. In order to avoid confusion, it should be noted that for a viewer facing in a distal direction and viewing the apparatus 28 as seen in FIG. 4, the viewer's left-hand and right-hand sides are the opposite of the actual left-hand and right-hand sides of the patient from the patient's point of view when the patient is lying on his back as shown in FIG. 1.

As noted, either or both of the angles 68 and 70 may in some cases be 90°. It is preferred, however, that each angle be less than 90° as described above.

As is apparent in FIG. 3, when the apparatus 28 is in place within the patient's blood vessel 24, the longitudinal axis 44 of the proximal portion of sheath 46 extending out of the perforation 30 is oriented at an acute angle 72 to a longitudinal axis 74 of the femoral artery 24. The acute angle 72 is in a range of from about 30° to about 60° and preferably is about 45°.

A preferred construction of the clamping plate 56 aids in holding the proximal portion of sheath 36 at the preferred angle 72. This is best understood with reference to FIG. 7. FIG. 7 is a view taken along line 7—7 of FIG. 4 showing an elevation view of the clamping plate 56. The clamping plate 56 has a substantially straight lower edge 76 located below the sheath 36. The clamping plate 56 has a lower skirt portion 78 between the straight lower edge 76 and the central axis 44 of sheath 36. The skirt portion has a height 80 and is located on the sheath 36 so as to support the proximal portion of sheath 36 at the angle 72 seen in FIG. 3 when the straight lower edge 76 engages the patient's skin 64 above the blood vessel 24 at approximately the location of the patient's right groin crease 26. The clamping plate 56 also includes a semi-circular upper portion 82.

FIG. 6 is an enlarged cross-sectional view of the sheath 36 taken along line 6—6 of FIG. 4. The sheath 36 has a longitudinal passage 84 defined therethrough from its proximal end 40 to its distal end 38. The sheath 36 also includes an inflation passage 86 and a treatment fluid passage 88.

An alternative design which could be used for the sheath 36 rather than having the thick wall with the two passages 86 and 88 disposed therein would be to construct the sheath 36 as a double-walled sheath with the annular space between walls divided into the necessary longitudinal passages 86 and 88.

The sheath apparatus 28 has first, second and third lateral arms 90, 92, and 94 extending therefrom. The first lateral arm 90 is communicated with longitudinal passage 84 and various fluids may be provided thereto by injection into port 96 defined on arm 90. The sealing balloon 46 can be inflated with either air, normal saline or contrast material in full or diluted concentration.

The second arm 92 is communicated with the inflation passage 86 and has a port 98 through which inflation fluid may be injected to inflate the sealing balloon 46. An indicator balloon 101 is mounted on second arm 92 and is also communicated with the inflation passage 86. The indicator balloon 101 is designed to inflate at a minimum pressure greater than a minimum pressure at which the sealing balloon 46 inflates, so that the indicator balloon 101 will always provide a visual indication of whether the sealing balloon 46 is fully inflated. If the indicator balloon 101 deflates, this indicates the sealing balloon 46 has or may soon deflate. So long as the indicator balloon 101 is inflated, this is a positive indication that the sealing balloon 46 is inflated.

The third arm 94 is communicated with the treatment fluid passage 88. The treatment fluid passage 88 is communicated at its distal end with a treatment fluid port 100 defined in the sheath 36 and communicating with the outer surface 42 thereof at a position located a distance 102 proximally from the sealing balloon 46. As is best seen in FIG. 3, the treatment fluid port 100 is arranged so that when the sheath 36 is received through an incision in the patient's body tissue 64, 62 and through the perforation 30 in the blood vessel 24, with the balloon 46 inflated inside the vessel 24 around the perforation 30 and with the vessel side wall 32 and overlying tissue 62, 64 sandwiched between the balloon 46 and the clamp 52, the treatment fluid port 100 is positioned between the balloon 46 and the clamp 52 and outside of the blood vessel 24. This allows the port 100 to deliver a treatment fluid to the wall of the artery and/or to the tissue surrounding the incision between the surface of the skin and the wall of the artery. The distance 102 of the treatment fluid port 100 from sealing balloon 46 is preferably in a range of from about 5 mm. to about 10 mm. The arm 94 has an external injection port 104 through which the treatment fluid is injected into the treatment fluid passage 88 and ultimately out the treatment fluid port 100.

Several different types of treatment fluid may be injected through the treatment fluid port 100 for different purposes.

A first possible use of treatment port 100 is to inject a contrast fluid which is visible on X-rays so as to indicate the flow of leaking blood around the perforation 30.

A second use for the treatment fluid port 100 is to inject a vaso-restrictive medication for inducing constriction of the vessel wall 32 around the sheath 36 at the perforation 30 to reduce leakage of blood through the perforation 30.

A third use for treatment port 100 is to inject a local anesthetic such as Lidocaine.

A conventional flap-type valve 103 is mounted at the proximal end of the sheath 36 through which catheters or other medical devices can be inserted.

It will now be readily apparent in viewing FIG. 3 how the apparatus 28 is used to reduce bleeding during vascular surgery.

The distal end portion of the sheath 36 is inserted through an incision in the patient's skin 64 and outlying tissue 62 and through a perforation 30 into the interior of the blood vessel 24 which preferably is the patient's right femoral artery. Then the sealing balloon 46 is inflated and the sheath 36 is pulled in a proximal direction until the sealing balloon 46 is engaged with the inside wall of the blood vessel 24 around the perforation 30. Then the clamp 52 is moved in a distal direction along the sheath 36 until it is snugly engaged against the patient's skin 64 thereby sandwiching the vessel wall 32 and overlying tissue 62 and 64 between the clamp 52 and the balloon 46. This compresses the inflated sealing balloon 46 against an annular area of the inside surface of the vessel wall 32 surrounding the perforation 30 and thus seals against the leakage of blood from the blood vessel 24 out through the perforation 30 around the sheath 36.

The preferred elliptical shape of the balloon 46 which is provided by orienting the balloon 46 at the angle 50 shown in FIG. 5 aids in placing the balloon 46 in a plane generally parallel to the longitudinal axis 74 of blood vessel 24 when the vascular sheath apparatus 28 is placed as shown in FIG. 3. The construction of the clamping device 52 is particularly adapted for use of the apparatus 28 in placing the sheath 36 in the femoral artery adjacent the patient's right groin crease. It will be appreciated, however, that in its broader aspects, the present invention may be utilized to provide a sealing sheath used in any of the patient's blood vessels.

The methods and apparatus of the present invention have been particularly adapted for use in placement of a sheath in the patient's right femoral artery since that is the preferred entrance point for many vascular surgery procedures. In approximately ten percent of patients, however, the patient's left femoral artery will be used as the entrance point at approximately the intersection with the patient's left groin crease. It will be appreciated that the preferred clamping device for use on the patient's left femoral artery would be a mirror image of the clamping device 52 described above.

It will be appreciated that the vascular sheath apparatus 28 is usable with any surgical procedure wherein a vascular sheath is needed to provide communication of medical devices with a patient's blood vessel. The particular apparatus 28 disclosed herein, however, is also particularly adapted for use with a suture placement device illustrated in FIGS. 8–33. The suture placement device is used to close the perforation 30 after the sheath apparatus 28 is withdrawn therefrom.

THE SUTURE DEVICE OF FIGS. 8–33

The vascular sheath apparatus 28 just described primarily addresses the problem of leakage of blood around the sheath while the sheath is in place through the perforation in the blood vessel. A second major problem with surgery of this type is bleeding through the perforation 30 after the surgical procedure is completed and the sheath is removed. This has typically been addressed by applying pressure to the location of the perforation for twenty to thirty minutes and then requiring the patient to lie immobile for many hours.

The suturing device of FIGS. 8–33 is designed to address this second problem of preventing bleeding through the perforation 30 after the sheath is removed therefrom.

Due to the fact that the blood vessel 24 lies below a substantial layer of tissue 62 and skin 64, it is not possible for the physician to suture the perforation 30 by any conventional technique. The present invention provides a means by which two suture threads may be attached to the blood vessel 24 on opposite sides of perforation 30 and then used to pull the perforation 30 closed.

FIG. 10 illustrates one of the suture threads designated by the numeral 106. The suture thread 106 has a suture point 108 attached to one end thereof.

The suture thread 106 is a conventional suture thread typically made of an absorbable material such as catgut.

The suture point is best shown in the enlarged views of FIGS. 12 and 13. Suture point 108 is constructed of a relatively hard material which can provide a sharp point 110 which can be driven through the side wall 32 of blood vessel 24 in a manner further described below. The suture point 108 also includes first and second flexible anchoring wings or barbs 112 and 114. As best seen in FIG. 13, the wings have a generally triangular shape when seen in elevation. The wings 112 and 114 are flexible so that they may move toward each other as the point 110 is driven through the side wall 32 of blood vessel 24. The wings 112 and 114 will then spread apart from each other when tension is placed upon the suture thread 106 so as to anchor the suture point 108 and prevent the suture point 108 from being pulled back through the side wall 32 of blood vessel 24. As is further described below, two of such suture threads and suture points will typically be used and will be placed on diametrically opposite sides of perforation 30 so that the suture threads 106 can then be pulled together to close the perforation 30.

The wings 112 and 114 have a length in a range of from about one-half millimeter to about five millimeters. They preferably have a somewhat curved configuration as shown in FIG. 12. This creates a very thin tip which easily penetrates the vessel wall 32 but which then spreads apart adequately so that retraction is difficult. The suture point 108 can be referred to as a combination suture point and anchor 108.

Several materials are suitable for suture points 108. One material is an absorbable organic catgut material which can be obtained in relatively stiff plate-like form. A second material is surgical stainless steel. A third material is a stiff material similar to Dacron or Teflon like that presently used to graft blood vessels.

FIG. 8 shows a plan view of a first embodiment of a carrier means 116 for carrying two of the suture points 108 and threads 106 in a distal direction through the longitudinal passage 84 of sheath 36 into the blood vessel 24, and for pulling the suture points 108 through the side wall 32 of the blood vessel 24 at circumferentially spaced positions about perforation 30.

The carrier means 116 includes an elongated carrier shaft 118 having a proximal end 120 and a distal end 122. Carrier means 116 includes first and second laterally extendable arms 124 and 126 connected to the distal end 122 of carrier shaft 118. As seen in FIG. 8, the shaft 118 has a reduced diameter distal portion from which both arms 124 and 126 protrude. It is also possible to provide two separate laterally spaced distal shaft portions (not shown), with each arm 124 or 126 being mounted on one of the distal shaft portions.

The shaft 118 has dimensions so that it fits relatively closely within the passageway 84 of sheath 36 thus insuring that the arms 124 and 126 are positioned substantially centrally within the sheath 36 so that each arm will spring outward to a location outside the periphery of perforation 30.

A rib 128 extends from shaft 118 in the same general plane as that in which the lateral arms 124 and 126 lie. Thus the rib 128 serves as an indicia means 128 for indicating to a surgeon viewing the proximal end 120 of carrier shaft 118 the orientation of the arms 124 and 126 which are hidden within the patient's body.

The shaft 118 is a hollow shaft having a shaft passage 130 defined therein. The arms 124 and 126 are also hollow and have arm passages defined therein which are communicated with the shaft passage 130.

FIG. 9 is a view similar to FIG. 8 showing a slightly modified alternative embodiment of the carrier means which is designated by the numeral 116A. The carrier means 116A differs in the shape of its first and second arms which are designated as 124A and 126A.

FIG. 11 shows a view of the carrier means 116A having first and second suture points 108 carried by the first and second laterally extendable arms 124A and 126A. The suture threads 106 run through the hollow arms 124A and 126A and through the passage 130 of shaft 118 and exit the proximal end 120 thereof as seen in FIG. 11.

Figure 26:
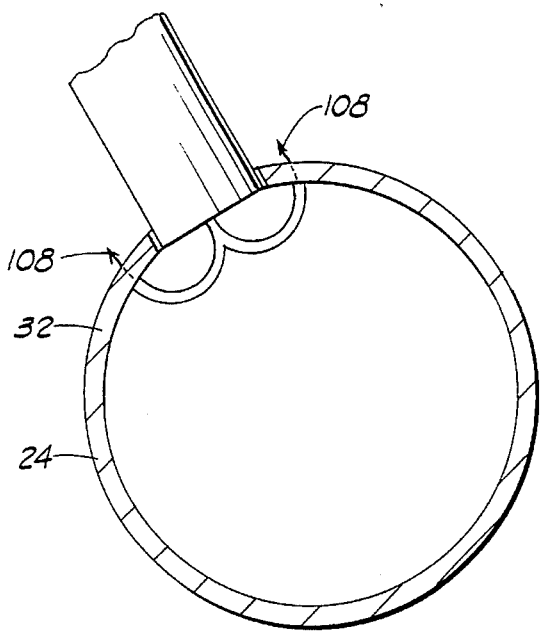

As best illustrated in the sequential series of FIGS. 25–28, the carrier means 116A is run through the central passage of sheath 36 into the interior of blood vessel 24 so that the lateral arms 124A and 126A extend laterally beyond the sheath 36 with the suture points 108 pointing in a proximal direction as seen in FIG. 25. Then, the sheath 36 and carrier means 116A are pulled in a proximal direction to pull the suture points 108 through the side wall 32 of blood vessel 24 as seen in FIG. 26.

Figure 27:
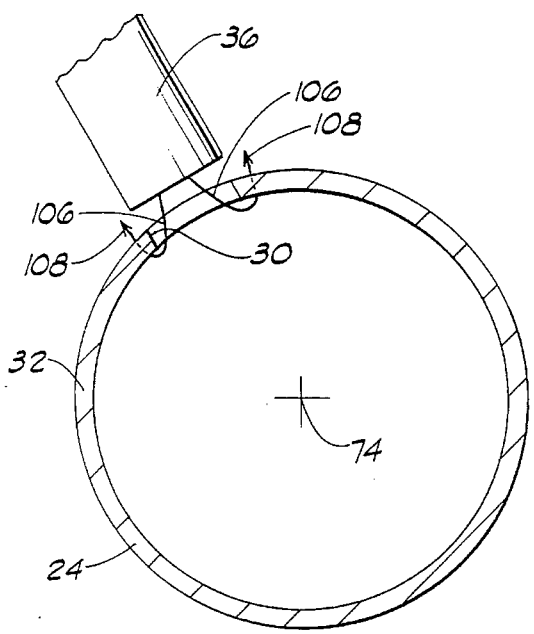

Then the carrier means 116A is withdrawn and sheath 36 is partially drawn away from the perforation 30 exposing the suture threads 106 as seen in FIG. 27.

As seen in FIG. 27, the suture points 108 penetrate the side wall 32 of blood vessel 24 so that the suture points 108 are located outside the side wall 32 with the suture threads 106 running through the side wall 32 into the blood vessel 24 and out through the outer sheath 36.

Subsequently, a perforation closing means such as perforation closing tube 132 is utilized to pull the suture points 108 laterally toward each other when a tension force is applied to the suture threads 106. The manner in which perforation closing means 132 and other alternative embodiments of perforation closing means are utilized as further described below.

To explain this procedure in more detail, it is first necessary to understand how the carrier means 116 or 116A with the suture threads mounted therein is inserted into the sheath 36. This is accomplished through the use of an intermediate insertion sheath means 134 shown in FIG. 14. The insertion sheath 134 provides a means for compressing the arms 124 and 126 to a laterally retracted position wherein they can be received in the longitudinal passageway 84 of outer sheath 36.

The intermediate insertion sheath 134 is a hollow, cylindrical member having a split 136 along its length. Insertion sheath 134 has an outside diameter slightly smaller than the dimensions of longitudinal passageway 84 of sheath 36 so that the insertion sheath 134 will fit within the longitudinal passageway 84 of outer sheath 36.

After the carrier means 116A has been loaded with suture points 108 and suture threads 106 as shown in FIG. 11, the arms 124A and 126A are deflected inwardly and placed within the intermediate insertion tube 134 in a manner like that generally illustrated in FIG. 19.

The intermediate insertion tube 134 with the retracted arms 124A and 126A received therein may then be inserted within the longitudinal passageway 84 of carrier 36 as illustrated in FIG. 20. Then the intermediate insertion sheath 134 can be pulled back out of the passageway 84 and peeled off the carrier means 116A thus leaving the carrier means 116A in place within the sheath 36 with the arms 124A and 126A in a retracted position as seen in FIG. 21.

Then the carrier means 116A is moved in a distal direction through the passageway 84 until a shoulder 138, which may also be referred to as a stop means 138 abuts the proximal end 40 of sheath 36. The relative dimensions of carrier means 116A and sheath 36 are such that when the shoulder 138 abuts sheath end 40 the arms 124A and 126A will extend distally beyond the distal end of sheath 36 so that they can spring back outward to an extended position wherein they extend laterally beyond the outside diameter of sheath 36 as shown in FIG. 22. The carrier means 116A can then be pulled in a proximal direction relative to the sheath 36 until the carrier arms 124A and 126A are located alongside the outer surface of sheath 36 as generally indicated in FIG. 25. Then the sheath 36 and carrier means 116A are pulled in a proximal direction as illustrated in FIG. 25 to drive the suture points 108 through the side wall 32 of blood vessel 24.

When pulling the suture points 108 through side wall 32, external pressure is applied with the clamping device 52. Typically, the sheath and carrier device are pulled approximately five to ten millimeters in the proximal direction to cause the suture points 108 to penetrate the wall 32.

Then sheath 36 and carrier means 116A are withdrawn as shown in FIG. 27. First the carrier means 116A is withdrawn from the sheath 36. The arms 126A and 124A are relatively flexible so that they can be uncurled and pulled back into the sheath 36 after the suture points 108 have been placed within the blood vessel 24.

FIGS. 23 and 24 illustrate a slightly modified version of sheath 36 which is designated as 36A. The sheath 36A has two diametrically opposed, generally L-shaped slots 140. The arms 124A and 126A will expand laterally outward through the long longitudinal legs of the slots 140 and then a slight rotation of the carrier means 116A will place the arms in the lower transverse legs of the slots 140 to aid in maintaining the rigidity of the arms 124A and 126A when they are used to pull the suture points 108 through the side wall 32 of blood vessel 24. FIG. 24 shows the arms 124A and 126A in their extended position as received in the shorter transverse legs of slots 140.

It will be appreciated that when using the embodiment of FIGS. 23 and 24 having the slots 140 cut in the sheath 36A, it is desirable to block or close the slots 140 prior to the time that the suture device 116A is to be used. This can be accomplished with a hollow, intermediate sheath 142 which is shown in place in FIG. 23 to block the slots 140. The sheath 142 must be withdrawn to uncover the slots 140 prior to use of the carrier means 116A.

After the suture points 108 have been placed through the side wall 32 of blood vessel 24 and the carrier means 116A has been withdrawn, as shown in FIG. 27, it is necessary to provide a means for pulling the suture threads 108 laterally toward each other to close the perforation 30. As is best appreciated in viewing FIG. 27, if one merely pulls upon the suture threads 106, they will pull in a generally parallel direction away from the perforation 30 and will not pull toward each other to close the perforation 30. It is not possible to simply pull laterally in opposite directions on the suture threads 106 because they must extend upward through the layer of fatty tissue 62 and skin 64.

Figure 28:
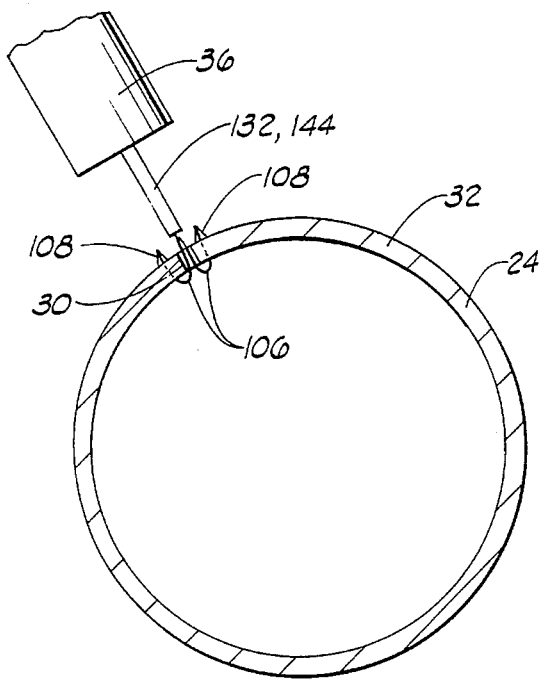

Thus, a perforation closing means such as the perforation closing tube 132 previously noted is used to aid in pulling the suture threads 106 together to close the perforation 30. The perforation closing tube 132 is shown in FIG. 18. It includes a distal portion 144 which will extend down through the skin 64 and tissue 62 to a position adjacent and just outside the perforation 30 as shown in FIG. 28. A proximal portion 146 of tube 132 is split as indicated 148 so that the suture threads 106 may be pulled laterally therefrom. When a tension force is applied to the suture threads 106 through the hollow tube 132, they will pull against the distal end of tube 132 and thus will pull laterally toward each other thus tending to pull the opposite sides of the side wall together to close the perforation 30 as schematically illustrated in FIG. 28.

Tube 132 is used in the following manner. Once the carrier means 116 is removed from the sheath 136, the two suture threads 106 are exposed and are firmly gripped by the left hand of the physician. The sheath 36 is then withdrawn a known distance so that the distal tip of sheath 36 lies on the outside of the vessel 24 as shown in FIG. 27. The fastening means such as tube 132 is then placed about the suture threads 106 and advanced into the sheath 36 to a position like that shown in FIG. 28. The position of the tube 132 is again known by measuring the depth to which it is inserted.

Also, the tube 132 may be constructed in a manner which further aids in pulling of the suture threads together by twisting of the tube. This is seen, for example, in the cross-sectional views of FIGS. 33A, 33B and 33C. These show three versions of tube 132 which are constructed for use with two, three and four suture threads, respectively.

In FIG. 33A, the tube 132A has first and second intersecting, parallel thread passages 139 and 141 defined therethrough for receiving two of the suture threads 106. When the tube 132A is moved to a position like that shown in FIG. 28, it may then be twisted to pull the suture threads 106 even closer together. Similarly, the fastening tube 132B of FIG. 33B is constructed for receiving three suture threads, and the fastening tube 132C of FIG. 33C is constructed for receiving four suture threads. As is further described below with regard to FIG. 30, carrier means may be provided for placing suture threads through the sheath one at a time, and it is possible to place more than two suture threads on a given perforation if that is needed to fully close the perforation.

Tube 132 is preferably constructed of a material which is absorbed by the human body, so that the tube 132 can be left in place.

Once the fastening device is in place, the injection of vaso-constrictive medications can be performed to insure that there is no bleeding from the perforation or surrounding area. The same medication can be injected earlier at the beginning of this whole procedure. The sheath 36 is then removed and the suture threads 106 can either be tied to the skin or simply cut off.

If the fastening tube 132 is utilized, the proximal portion of the tubing 132 protruding outside the skin can simply be cut off after the suture threads have been pulled laterally through the splits 148. The tubing 132 is then sutured to the skin or it can be affixed to the skin using various clips or buckles.

Another perforation closing means which can be used instead of or with the perforation closing tube 132 is illustrated in FIGS. 15–17.

FIG. 15 shows a plan view of a fastening disc generally designated by the numeral 150. The disc 150 is preferably constructed from a material absorbable by the human body such as a plate-like piece of hard organic material of the type used for sutures. The fastening disc has an opening 152 defined therein through which the suture threads 106 are to be run. Opening 152 has tapered sides which lead to corners such as 154. The fastening disc is of such a size that it can be run down through the longitudinal passageway 84 of outer sheath 36 to a position adjacent the exterior surface of side wall 32 of blood vessel 24. The suture threads 106 will be received in the corners 154 in a wedge-like fashion when tension is placed on the suture threads 106. The relatively small dimensions of the opening 152 will cause the suture threads 106 to be pulled toward each other when tension is placed on suture threads 106 and when the fastening disc 150 is located adjacent the perforation 30.

The fastening disc could also be circular in configuration. It has a thickness of approximately one millimeter.

The hollow tube 132 can be used to push the fastening disc 150 distally through the outer sheath 36 and to hold the same in place while tension is applied to the suture threads 106.

As shown in FIG. 16, which is a cross-sectional view, the fastening disc 150 has a distally facing side 156. The disc has wings 158 and 160 which in their relaxed position extend distally as seen in FIG. 16. When tension is applied to the suture threads 106 and those suture threads are wedged in the corners 154 of opening 152, the disc 150 will tend to flatten out to a position like that shown in FIG. 17 thus providing a spring-like action to help maintain the tension in the suture threads 106.

As the wings 158 and 160 of the fastening disc 150 bend outward toward the position of FIG. 17, it tends to close the corners 154 thus more tightly gripping the suture threads 106.

Although the carrier means 116 disclosed herein is constructed for simultaneously carrying two suture points and suture threads into position, it will be appreciated that in some of the broader aspects of the present invention, the two suture points could be individually carried into place.

Although the two suture points 108 are preferably placed at diametrically opposite positions on the side wall 32 of perforation 30 it will be understood that more generally speaking they can be described as being placed at circumferentially spaced positions around the perforation 30.

Another difference between the embodiments of the carrier means 116 of FIG. 8 and the carrier means 116A of FIG. 9 is the relative longitudinal position of the ends of the arms 124 and 126. In the embodiment of FIG. 8, it is noted that the free ends of arms 124 and 126 are longitudinally spaced from each other and thus would carry the suture points 108 at longitudinally spaced positions along carrier 116. That arrangement is preferable when the suture points 108 are placed along a line generally parallel to the longitudinal axis 74 of blood vessel 24.

In FIGS. 25–28, the suture points 108 have been shown as being placed on diametrically opposite sides of perforation 30 with the suture points 108 aligned in a line generally perpendicular to the longitudinal axis 74 of blood vessel 24. In some instances, however, that orientation may be undesirable since it may tend to constrict the diameter of the blood vessel 24 as the perforation 30 is pulled closed.

A preferred orientation is that just described with regard to FIG. 8 wherein the suture points 108 are aligned substantially parallel to the longitudinal axis 74, so that when they are pulled together there will not be any narrowing of the diameter of blood vessel 24. By staggering the longitudinal position of the free ends of arms 124 and 126, the carrier means 116 can be placed at an angle like the angle of sheath 36 shown in FIG. 3 and can then be pulled into substantially simultaneous engagement with the vessel wall 32.

FIGS. 29–31 illustrate several alternative embodiments of carrier means.

FIG. 29 is a view similar to the lower portion of FIG. 19 and illustrates a preferred manner in which the flexible arms 124A and 126A may be folded into the bore of insertion tube 134. By folding the arms 124A and 126A in the manner illustrated in FIG. 29, rather than the manner illustrated in FIG. 19, the arms can be constructed of physically larger size since they extend across the entire inside diameter of tube 134.

FIG. 30 illustrates an alternative carrier means generally designated by the numeral 160. Carrier means 160 has a single flexible arm 162, and has a two-piece shaft comprised of a distal shaft portion 164 and a proximal shaft portion 166 joined together at shaft connection 168. Shaft connection 168 may either be a threaded connection or a snap-type connection. It does, however, need to be arranged so that the radial orientation of the components attached to the shaft portions 164 and 166 will always be in the relative position shown in FIG. 30.

A centralizer means 169 is defined on the distal shaft portion 164. Centralizer means 169 is a cylindrical part which will be closely received within the bore of the insertion tube 134 or the alternative insertion tube of FIG. 32. As is apparent in FIG. 30, the shaft 164, 166 is eccentrically placed on the centralizer 169 so that the flexible arm 162 reaches out across the centralizer 169.

A stop means 170 extends from proximal shaft portion 166 in the same plane in which the arm 162 lies. Also, a handle 172 extends from proximal shaft portion 166 in the same plane in which the stop means 170 and arm 162 lie.

The carrier means 160 of FIG. 30 may be used to place multiple suture threads, one at a time in sequential order, through the sheath.

The carrier means 160 is also particularly constructed for use with an alternative insertion sheath 174 illustrated in FIG. 32. The insertion sheath 174 is a hollow cylindrical sheath having a valve means 176 on its proximal end. The valve means 176 may either be a conventional split diaphragm type valve like that illustrated in FIG. 19, or it may be a variable constriction valve of the type referred to as a Tui Borst valve which has an opening of variable diameter which can be restricted by rotating the valve member 176.

If the alternative insertion sheath 174 of FIG. 32 is utilized instead of insertion sheath 134 in the sequential series of FIGS. 19–21, the insertion sheath 174 will remain in place within the outer sheath 36 throughout the entire procedure, and the valve means 176 is utilized to minimize bleeding through the insertion sheath 174.

When utilizing the insertion sheath 174 having the valve means 176 it is necessary to provide a means to assemble the suture carrier therewith without having to insert the flexible arms and centralizer such as arm 162 and centralizer 169 through the valve apparatus 176. This can be accomplished with the two-piece carrier means 160 of FIG. 30 by disconnecting the distal and proximal portions 164 and 166 thereof at connection 168. Then the distal portion 164 can be inserted in a distal end 178 of introduction sheath 174, until the small shaft portion 164 proximal of centralizer 169 extends through the valve 176. Then the proximal shaft portion 166 may be made up to the distal shaft portion 164 at connection 168.

The stop means 170 will abut the proximal end 180 of insertion sheath 174, and the shaft 164 is of such a length that the flexible arm 162 will be located approximately in the position of arm 124A as seen in FIG. 22 extending out slightly beyond the end of sheath 36.

FIG. 31 illustrates an alternative double-armed carrier means 180 constructed similarly to the single-arm carrier means 160 of FIG. 30. Carrier means 180 includes a centralizer 182, a distal shaft portion 184, a proximal shaft portion 186, a shaft connection 188, a stop means 190, a handle 192, and first and second flexible arms 194 and 196. Carrier means 180 is also particularly useful with an introduction sheath 174 like that of FIG. 32 wherein the shaft connection 188 allows the carrier to be broken apart for assembly with the introduction sheath 174 having the valve means 176.

THE ALTERNATIVE SHEATH HAVING AN ACCORDION FOLD OF FIGS. 34–37

Figure 34:
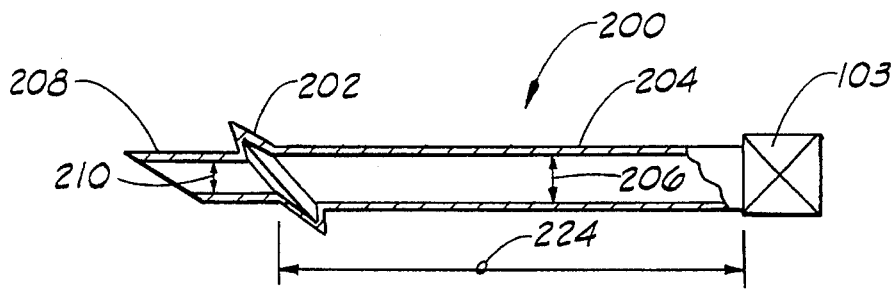
FIG. 34 is a plan, partially sectioned view of an alternative embodiment of the carrier sheath having an accordion fold defined therein to provide a sealing means.
Figure 35:
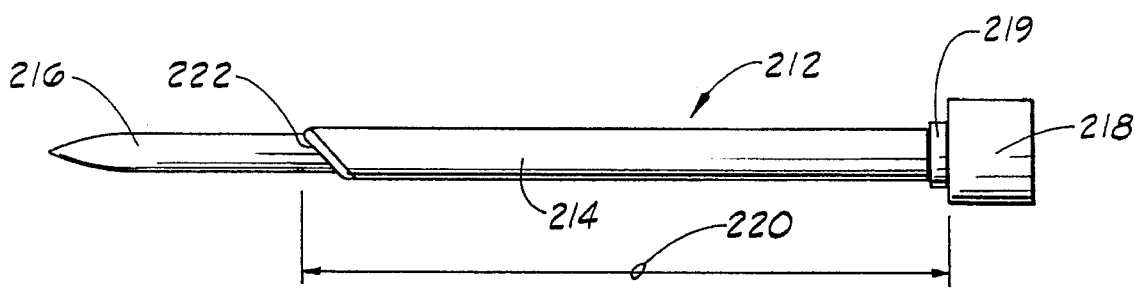
FIG. 35 is a plan view of a dilator for use with the carrier sheath of FIG. 34.

FIG. 34 schematically illustrates a plan, partially cross-section view of an alternative embodiment of a sheath similar to the sheath 36 of FIG. 4. The sheath of FIG. 34 is designated by the numeral 200, and it will be appreciated that the sheath 200 is shown in much more schematic fashion than is the sheath 36 of FIG. 4. The details of construction of the sheath 200, however, are substantially identical to the sheath 36 of FIG. 4 except for the fact that the inflatable balloon 46 of FIG. 4 has been replaced with an accordion fold 202 seen in FIG. 34.

The sheath 200 will have a valve like valve 103 of FIG. 4 on the proximal end thereof and will also have the various arms and ports such as arms 90, 92 and 94 which have been deleted for clarity of illustration.

Figure 36:
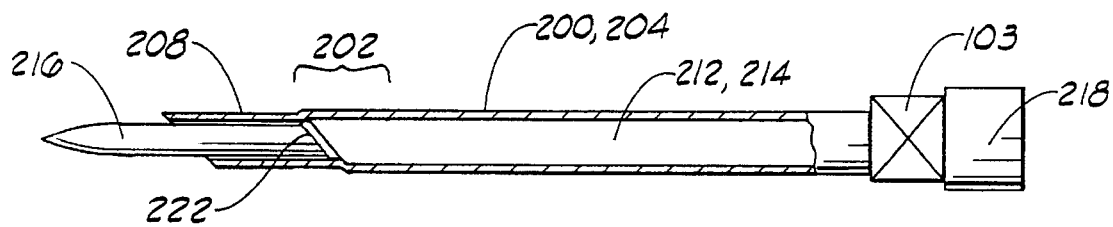
FIG. 36 is a plan, partially sectioned view of the dilator of FIG. 35 in place within the sheath of FIG. 34 to move the accordion fold to a radially retracted position.

The accordion fold 202 is seen in FIG. 34 in its radially expanded position and is seen in FIG. 36 in its radially contracted position.

The sheath 200 is preferably constructed of a plastic material which is relatively flexible and is a resilient memory-retaining material. The sheath 200 is preferably constructed so that when the material thereof is in its natural relaxed state, the accordion fold 202 returns to the radially expanded position illustrated in FIG. 34. Also, the accordion fold 202 may be constructed of a different material than that used to construct the remainder of sheath 200. It may be desirable to construct accordion fold 202 of a material having a higher coefficient of friction with body tissue than does typical plastic sheath material.

The sheath 200 is divided by the accordion fold 202 into a proximal portion 204 having an inside diameter 206, and a distal portion 208 having an inside diameter 210. The diameter 206 is greater than the diameter 210.

A dilator 212 provides a means for maintaining the accordion fold 202 in its radially retracted position of FIG. 36 as the sheath 200 is inserted through a perforation in a blood vessel. Dilator 212 includes a proximal portion 214 and a distal portion 216 each having an outside diameter slightly less than diameter 206 and 210, respectively. Portions 214 and 216 are joined by step 222. Dilator 212 has a handle 218 on its proximal end and has a snap lock 219 defined thereon which will lock within position when engaged with the valve 103.

The proximal portion 214 of dilator 212 has a length 220 from handle 218 to the step 222 which is greater than a length 224 seen in FIG. 34 for the proximal portion 204 of sheath 200 when the accordion fold 202 is in its expanded position.

When the dilator 212 is inserted into the sheath 200 as shown in FIG. 36, the step 222 catches against the distal portion 208 of sheath 200 and causes the accordion fold 202 to be stretched out and moved to a radially retracted position as seen in FIG. 36. Then the sheath 200 can be inserted into a perforation in the patient's blood vessel. Similarly, the dilator 212 will be utilized to remove the sheath 200 from the patient's blood vessel.

Figure 37:
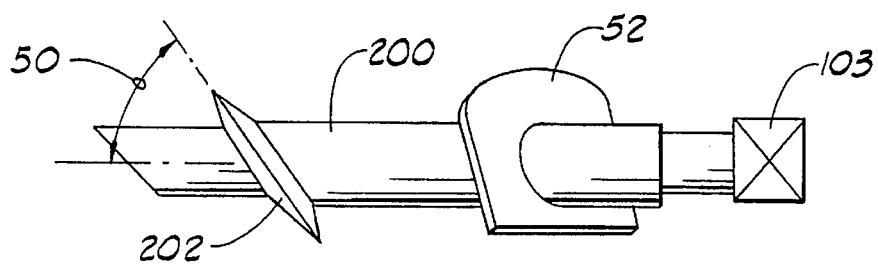
FIG. 37 is a plan view of the sheath of FIG. 34 with a sliding clamp assembled therewith.

As schematically illustrated in FIG. 37, the sheath 200 will preferably be used with a sliding clamp 52 like that previously described.

The sheath 200 with accordion fold 202 is used in the following manner.

First, a perforation is preferably formed in the patient's blood vessel with a predilator as is known to the art. The predilator will preferably have a size one French greater than the outside diameter of proximal portion 204 of sheath 200.

Then after predilation, the dilator 212 is inserted in sheath 200 as shown in FIG. 36 and then the sheath 200 and dilator 212 are inserted through the previously formed perforation in the patient's artery. The dilator 212 holds the accordion fold 202 in its radially retracted position until the accordion fold 202 is received within the patient's blood vessel.

Then, the dilator 212 is removed and the resilient memory of the sheath 200 will cause the accordion fold 202 to move back to its radially expanded position as seen in FIG. 34, with the accordion fold 202 located inside the patient's blood vessel.

Then the accordion fold 202 is snugged up against the inside wall of the blood vessel around the perforation utilizing the clamp 52 in a manner substantially identical to that described above with reference to FIG. 3 in connection with the inflatable balloon 46.

As seen in FIG. 37, the accordion fold 202 is preferably placed at the same angle 50 as previously noted with regard to FIG. 5.

It will be appreciated that in its broader aspects, the invention of the sheath 200 with accordion fold 202 could be utilized without the sliding clamp 52 so as to simply utilize the accordion fold 202 in place of an inflatable balloon.

Thus it is seen that the apparatus and methods of the present invention readily achieve the ends and advantages mentioned as well as those inherent therein. While certain preferred embodiments of the invention have been illustrated and described for purposes of the present disclosure, numerous changes may be made by those skilled in the art which changes are encompassed within the scope and spirit of the present invention as defined by the appended claims.

What is claimed is:

1. An apparatus for suturing a perforation in a side wall of a patient's blood vessel, comprising:

an outer sheath having a longitudinal passage defined therethrough, said outer sheath being insertable through the perforation in the patient's blood vessel;

a first combination suture point and anchor;

a first suture thread connected to said first combination suture point and anchor;

carrier means for carrying said first combination suture point and anchor in a distal direction through said longitudinal passage of said outer sheath into the patient's blood vessel and for pulling said first combination suture point and anchor in a proximal direction through the side wall of the patient's blood vessel so that said first combination suture point and anchor is anchored against being pulled back through said side wall in a distal direction;

a second combination suture point and anchor;

a second suture thread connected to said second combination suture point and anchor; and wherein said carrier means further provides a means for carrying said second combination suture point and anchor in said distal direction through said longitudinal passage of said outer sheath into the patient's blood vessel and for pulling said second combination suture point and anchor in said proximal direction through the side wall of the patient's blood vessel at a circumferentially spaced position around said perforation from said first combination suture point and anchor.

2. The apparatus of claim 1, further comprising:

perforation closing means for pulling said combination suture points and anchors laterally toward each other when a tension force is applied to said suture threads after said combination suture points and anchors are placed through the side wall.

3. The apparatus of claim 1, wherein said carrier means comprises:

an elongated carrier shaft having a proximal end and a distal end; and first and second laterally extendable arms connected to said distal end of said carrier shaft, said first and second combination suture points and anchors being carried by said first and second arms, respectively.

4. The apparatus of claim 3, wherein:

said arms are extendable from a retracted position wherein said arms are received in said longitudinal passage of said outer sheath, to a laterally extended position wherein said arms extend laterally beyond said sheath.

5. The apparatus of claim 3, further comprising:

indicator means, located on said shaft, for indicating an orientation of said arms within the blood vessel to a physician viewing said proximal end of said shaft.

6. The apparatus of claim 3, wherein:

said arms are resilient so that they are extendable from a retracted position wherein said arms are received in said longitudinal passage of said sheath with said arms pointing in a proximal direction, to a laterally extended position wherein said arms extend laterally beyond said sheath.

7. The apparatus of claim 3, wherein:

said first combination suture point and anchor is carried at a position longitudinally spaced from said second combination suture point and anchor so that said first and second combination suture points and anchors can substantially simultaneously penetrate the side wall of the patient's blood vessel with said sheath and said carrier means oriented at an acute angle to a longitudinal axis of the patient's blood vessel.

8. The apparatus of claim 1, wherein said carrier means comprises:

an elongated carrier shaft having a proximal end and a distal end; and a first laterally extendable arm connected to a distal portion of said shaft, said first combination suture point and anchor being carried by said first arm.

9. The apparatus of claim 8, wherein:

said first arm is hollow and has an arm passage extending therethrough; and said first suture thread extends through said arm passage of said first arm.

10. The apparatus of claim 9, wherein:

said carrier shaft has a longitudinal shaft passage defined therein and communicated with said arm passage, and said first suture thread extends through said shaft passage.

11. The apparatus of claim 8, wherein:

said carrier shaft has a longitudinal shaft passage defined therein, and said first suture thread extends through said shaft passage.

12. The apparatus of claim 8, wherein:

said carrier shaft has a stop abutment defined thereon and located so as to abut a proximal end of said outer sheath after said arm has moved to a laterally extended position.

13. The apparatus of claim 8, wherein:

said carrier shaft has a centralizer defined thereon and constructed to be closely received in said longitudinal passage of said outer sheath to position said first laterally extendable arm radially relative to a longitudinal axis of said outer sheath.

14. The apparatus of claim 1, further comprising:

indicator means, located on said carrier means, for indicating an orientation of said first and second combination suture point and anchor within the blood vessel to a human operator of said apparatus.

15. The apparatus of claim 1, wherein:

said combination suture point and anchor includes a barb.

16. The apparatus of claim 1, wherein:

said first combination suture point and anchor includes flexible anchoring wings.

17. The apparatus of claim 1, wherein:

said each combination suture point and anchor is constructed of a material absorbable by the human body.

18. The apparatus of claim 1, wherein:

each said combination suture point and anchor is constructed of a metal.

19. The apparatus of claim 1, wherein said first combination suture point and anchor is anchored to the side wall of the blood vessel.

20. An apparatus for suturing a perforation in a side wall of a patient's blood vessel, comprising:

an outer sheath having a longitudinal passage defined therethrough, said outer sheath being insertable through the perforation in the patient's blood vessel;

a first combination suture point and anchor;

a first suture thread connected to said first combination suture point and anchor;

carrier means for carrying said first combination suture point and anchor in a distal direction through said longitudinal passage of said outer sheath into the patient's blood vessel and for pulling said first combination suture point and anchor in a proximal direction through the side wall of the patient's blood vessel so that said first combination suture point and anchor is anchored against being pulled back through said side wall in a distal direction;

a second combination suture point and anchor;

a second suture thread connected to said second combination suture point and anchor; and wherein said carrier means is a means for simultaneously carrying both said first and second combination suture points and anchors.

21. The apparatus of claim 20, wherein said first combination suture point and anchor is anchored to the side wall of the blood vessel.

22. An apparatus for suturing a perforation in a patient's blood vessel, comprising:

an outer sheath having a longitudinal passage defined therethrough, said outer sheath being insertable through the perforation in the patient's vessel;

a suture carrier insertable through said longitudinal passage of said outer sheath, said carrier including:

an elongated carrier shaft having a proximal end and a distal end; and first and second laterally extendable arms connected to said distal end of said carrier shaft, said arms being extendable from a retracted position wherein said arms are received in said longitudinal passage of said outer sheath, to a laterally extended position wherein said arms extend laterally beyond said outer sheath;

first and second suture points detachably mounted on said first and second arms, respectively, said suture points being pointed in a proximal direction when said arms are in their laterally extended position; and first and second suture threads connected to said first and second suture points, respectively.

23. The apparatus of claim 22, further comprising:

means for inserting said arms, with said suture points mounted thereon, into said longitudinal passage of said outer sheath.

24. The apparatus of claim 22, wherein said suture carrier provides means for pulling said first and second suture points so that said suture points are thereby moved relative to the patient's blood vessel and engage and anchor to a side wall of the blood vessel adjacent the perforation in the blood vessel.

25. An apparatus for suturing a perforation in a side wall of a patient's blood vessel, comprising:

an outer sheath having a longitudinal passage defined therethrough, said outer sheath being insertable through the perforation in the patient's blood vessel;

first and second suture points;

first and second suture threads connected to said first and second suture points, respectively;

carrier means for carrying said first and second suture points in a distal direction through said longitudinal passage of said outer sheath into the patient's blood vessel and for pulling said first and second suture points in a proximal direction through the side wall of the patient's blood vessel at circumferentially spaced positions around the perforation;

wherein said carrier means includes an elongated carrier shaft having a proximal end and a distal end, and said carrier means includes first and second laterally extendable arms connected to said distal end of said carrier shaft, said first and second suture points being carried by said first and second arms, respectively; and wherein said outer sheath has a side wall with first and second guide slots defined therethrough for receiving said first and second arms, respectively, when said arms move to said extended position.

26. The apparatus of claim 25, further comprising:

a removable hollow inner sheath receivable in said longitudinal passage of said outer sheath when said carrier means is removed from said outer sheath, said inner sheath blocking said guide slots.

27. An apparatus for suturing a perforation in a side wall of a patient's blood vessel, comprising:

an outer sheath having a longitudinal passage defined therethrough, said outer sheath being insertable through the perforation in the patient's blood vessel;

first and second suture points;

first and second suture threads connected to said first and second suture points, respectively;

carrier means for carrying said first and second suture points in a distal direction through said longitudinal passage of said outer sheath into the patient's blood vessel and for pulling said first and second suture points in a proximal direction through the side wall of the patient's blood vessel at circumferentially spaced positions around the perforation;

wherein said carrier means includes an elongated carrier shaft having a proximal end and a distal end, and said carrier means includes first and second laterally extendable arms connected to said distal end of said carrier shaft, said first and second suture points being carried by said first and second arms, respectively; and intermediate insertion sheath means for compressing said arms to a laterally retracted position and for inserting said arms into said longitudinal passage of said outer sheath.

28. An apparatus for suturing a perforation in a side wall of a patient's blood vessel, comprising:

an outer sheath having a longitudinal passage defined therethrough, said outer sheath being insertable through the perforation in the patient's blood vessel;

a first suture point;

a first suture thread connected to said first suture point;

carrier means for carrying said first suture point in a distal direction through said longitudinal passage of said outer sheath into the patient's blood vessel and for pulling said first suture point in a proximal direction through the side wall of the patient's blood vessel;

said carrier means including:
an elongated carrier shaft having a proximal end and a distal end; and
a first laterally extendable arm connected to a distal portion of said shaft, said first suture point being carried by said first arm; and intermediate insertion sheath means for compressing said arm to a laterally retracted position and for inserting said arm into said longitudinal passage of said outer sheath.

29. The apparatus of claim 28, wherein:

said intermediate insertion sheath means is a split cylinder which can be peeled off said carrier means after insertion of said arm into said longitudinal passage of said outer sheath.

30. The apparatus of claim 28, wherein:

said intermediate insertion sheath means includes a valve means on a proximal end thereof for reducing seepage of blood past said carrier means.

31. The apparatus of claim 30, wherein:

said carrier shaft is a two-piece shaft including a distal portion and a proximal portion joined together at a shaft connection so that said distal portion may be inserted into a distal end of said intermediate insertion sheath means and then connected at said shaft connection to said proximal portion.

32. An apparatus for suturing a perforation in a patient's blood vessel comprising:

an outer sheath having a longitudinal passage defined therethrough, said outer sheath being insertable through the perforation in the patient's vessel;

a suture carrier insertable through said longitudinal passage of said outer sheath, said carrier including:
an elongated carrier shaft having a proximal end and a distal end; and
first and second laterally extendable arms connected to said distal end of said carrier shaft, said arms being extendable from a retracted position wherein said arms are received in said longitudinal passage of said outer sheath, to a laterally extended position wherein said arms extend laterally beyond said outer sheath;

first and second suture points detachably mounted on said first and second arms, respectively;

first and second suture threads connected to said first and second suture points, respectively; and perforation closing means for pulling said suture points laterally toward each other when a tension force is applied to said suture threads after said suture points have penetrated a side wall of the patient's blood vessel.

33. A method of closing a perforation in a side wall of a patient's blood vessel upon removal of a vascular sheath from the perforation, comprising:

(a) providing first and second suture threads having first and second suture points connected thereto, respectively;

(b) carrying said first and second suture points, in a distal direction through said vascular sheath into said blood vessel;

(c) penetrating the side wall of the blood vessel in a proximal direction with said suture points so that said suture points are located outside the side wall with said suture threads running through the side wall into the blood vessel and out through said vascular sheath;

(d) removing said vascular sheath from the perforation; and (e) closing the perforation with said suture threads.

34. The method of claim 33, wherein:

in step (c), said first and second suture points penetrate the side wall at first and second locations, respectively, on diametrically opposite sides of the perforation, said first and second locations being aligned substantially parallel to a longitudinal axis of the blood vessel.

35. The method of claim 34, wherein:

in step (e), the perforation is closed without any substantial constriction of said blood vessel.

36. The method of claim 33, wherein step (e) comprises:

(e)(1) applying a tension force to said first and second suture threads; and (e)(2) converting said tension force to a lateral force closing the perforation.

37. The method of claim 36, wherein:

in step (e) (2), said lateral force is in a direction substantially parallel to a longitudinal axis of the blood vessel.

38. The method of claim 33, wherein:

step (b) is performed with a carrier device inserted in a distal direction through said vascular sheath; and step (c) is performed by pulling said carrier device in a proximal direction while applying a compressive force to the patient's skin exterior of the blood vessel.

39. The method of claim 33, wherein:

in step (b) said first and second suture points are carried through said vascular sheath simultaneously.

40. The method of claim 33, wherein:

in step (b) said first and second suture points are carried through said vascular sheath sequentially, one after the other.

41. The method of claim 33, wherein in step (c) said suture points engage the side wall so that said suture points anchor thereto.

* * * * *